(12) United States Patent
Bouhour et al.

(10) Patent No.: US 6,408,209 B1
(45) Date of Patent: Jun. 18, 2002

(54) ENSLAVED ACTIVE IMPLANTABLE MEDICAL DEVICE PROTECTED FROM THE EFFECTS OF BRADY-AND/OR TACHY-DEPENDENT EXTRASYSTOLES

(75) Inventors: Anne Bouhour, Ville d'Avray; Marcel Limousin, Paris; Jean-Luc Bonnet, Montrouge, all of (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 09/616,272

(22) Filed: Jul. 14, 2000

(30) Foreign Application Priority Data

Jul. 15, 1999 (FR) .......................................... 99 09165

(51) Int. Cl.$^7$ ................................................ A61N 1/36
(52) U.S. Cl. ............................................. 607/19; 607/25
(58) Field of Search ........................ 607/9, 11, 14–15, 607/17, 19–20; 600/508–510, 515, 518–519

(56) References Cited

U.S. PATENT DOCUMENTS

| | | | |
|---|---|---|---|
| 5,271,394 A | 12/1993 | Girodo et al. ............... | 607/15 |
| 5,306,293 A | 4/1994 | Zacouto ....................... | 607/17 |
| 5,312,451 A | 5/1994 | Limousin et al. ............. | 607/15 |
| 5,622,428 A | 4/1997 | Bonnet ......................... | 128/630 |
| 5,645,576 A | 7/1997 | Limousin et al. ............. | 607/19 |
| 5,713,928 A | 2/1998 | Bonnet et al. ................ | 607/9 |
| 5,722,996 A | 3/1998 | Bonnet et al. ................ | 607/17 |
| 5,766,228 A | 6/1998 | Bonnet et al. ................ | 607/16 |
| 5,938,687 A * | 8/1999 | Bouhour et al. .............. | 607/15 |
| 6,052,616 A * | 4/2000 | Bonnet et al. ................ | 600/515 |
| 6,161,041 A * | 12/2000 | Stoop et al. ................... | 607/14 |

FOREIGN PATENT DOCUMENTS

| | | | | |
|---|---|---|---|---|
| EP | 0 672 433 A1 | 9/1995 | .......... | A61N/1/365 |
| EP | 0 755 696 A2 | 1/1997 | .......... | A61N/1/368 |
| EP | 0 755 696 A3 | 5/1998 | .......... | A61N/1/368 |

* cited by examiner

*Primary Examiner*—Kennedy Schaetzle
*Assistant Examiner*—Kristen Droesch
(74) *Attorney, Agent, or Firm*—Orrick, Herrington & Sutcliffe LLP

(57) ABSTRACT

A rate-responsive active implantable medical device, in particular a cardiac pacemaker, defibrillator or cardiovertor, which is protected from the effects of bradycardia- and/or tachycardia-dependent extrasystoles. The device is able to stimulate at least one cardiac cavity by delivering low-energy pulses to the heart at a frequency determined by the device, and evaluates the activity level of the patient bearing the device and discriminates between phases of rest, normal activity and effort. Further, the device is capable of adjusting the frequency according to the determined activity level, more particularly decreasing the base frequency to a given minimum level during a rest phase. The device also detects the occurrence of brady-dependent extrasystoles, determines a corresponding extrasystole rate, and then increases the base frequency minimum level when the extrasystole rate exceeds a predetermined threshold during the rest phase. In a similar manner, tachy-dependent extrasystoles are diagnosed and the stimulation rate maximum is adjusted (reduced). These adjustments inhibit the appearance of extrasystoles.

10 Claims, 1 Drawing Sheet

US 6,408,209 B1

ENSLAVED ACTIVE IMPLANTABLE MEDICAL DEVICE PROTECTED FROM THE EFFECTS OF BRADY-AND/OR TACHY-DEPENDENT EXTRASYSTOLES

FIELD OF THE INVENTION

The present invention relates to "active implantable medical devices" as defined by the Jun. 20, 1990 Directive No. 90/385/CEE of the Council of the European Communities, more particularly to pacemakers, defibrillators and/or cardiovertors which are capable of delivering low-energy stimulation pulses to the heart for treatment of heart (cardiac) rate disorders. The invention also relates to the prevention of consequences which extrasystoles can have on the operation of such devices.

BACKGROUND OF THE INVENTION

Extrasystoles, the appearance of an extra spontaneous contraction of a cardiac chamber out of the normal sequence and rhythm, are known. They can be either ventricular in origin (VES) or atrial in origin (AES).

There are two types of VES extrasystoles. The first VES type corresponds to a ventricular detection (i.e., the sensing or "detection" of a spontaneous ventricular contraction) or ventricular stimulation (i.e., a low-energy stimulation pulse delivered by the device in the ventricle) that is not preceded by an atrial event (i.e., either an atrial detection or a stimulation delivered by the device in the atrium) in an interval of time considered to be physiological. A physiological time interval refers to the time following an atrial event when a ventricular event should occur to be physiologically healthy to a patient, for example, an interval ranging between 31 and 300 ms. A second VES type corresponds to a ventricular detection that is preceded by an atrial event in an interval of time ranging between 31 and 300 ms, if the atrio-ventricular time (i.e., the time occurring between the atrial event and the following ventricular detection) of the examined cycle is at least 31 ms less than the atrio-ventricular time of the preceding cardiac cycle. The "cardiac cycle" is defined as the interval of time between two events of a comparable nature in the same cardiac cavity.

An AES-type extrasystole corresponds to a "P wave" (also called a "P event", i.e., a detection of spontaneous activity having its origin in an atrium) following the P wave of the preceding atrial event, within an interval that is less than a fraction of the average interval of the atrial frequency, calculated over an average of a number, e.g., eight, of cardiac cycles not including an extrasystole. The atrial frequency is the cardiac rate as measured based on successive atrial events. The cardiac rate may be measured in terms of a frequency of beats per minute (bpm).

In practice, all patients present a certain number of isolated VES or AES events without suffering any adverse consequence. But when these extrasystoles become too frequent, typically, more than ten VES or AES events per minute, this phenomenon can impair the filling of the heart cavities with blood, and affect the hemodynamic function of the heart. Furthermore, such phenomenon can induce heart-rate disorders.

The frequency at which either AES or VES events are manifested is determined by a parameter known as the "extrasystole rate". This parameter increases when the frequency at which either AES or VES events appear increases.

In certain patients, the appearance of a high extrasystole rate can be related to a heart rate level that is either too low (i.e., a "brady-dependent extrasystole"), or a heart-rate level that is too high (i.e., a "tachy-dependent extrasystole").

The inventors have discovered that, when a stimulation frequency is determined by the device according to the patient's activity or cardiac output requirements (i.e., the device is an enslaved (also called a rate-responsive) device which determines a stimulation frequency as a function of a physiological and/or a physical parameter indicative of the patient's level of activity), the appearance of brady-dependent or tachy-dependent extrasystoles can, in certain cases, result in an undesirable phenomenon of oscillation and instability of the stimulation frequency control algorithm. This phenomenon appears most particularly in devices equipped with a control function known as a "rest frequency algorithm" as described, for example, in EP-A-0 672 433 and the corresponding U.S. Pat. No. 5,645,576, commonly assigned to the assignee hereof ELA Médical. This algorithm adjusts the base stimulation frequency to the activity of the patient, and, in particular, lowers the base stimulation frequency to a minimum frequency limit in the case of an extended period of rest (i.e., a "rest phase") exhibited by the patient. The minimum frequency limit reached during an extended rest period is often called the "sleep frequency".

When the patient is prone to brady-dependent extrasystoles, an "oscillation" phenomenon can be observed as follows. First, in the case of an extended rest period, the base stimulation frequency of the patient is lowered until the base stimulation frequency reaches the initial sleep frequency. This low frequency then induces extrasystoles. As a result, the rest frequency control algorithm, which has a built-in monitoring function, diagnoses the presence of a sufficiently large extrasystole condition and then increases the base stimulation frequency to above the range that induces extrasystoles. Then, because the device also detects any prolonged rest period, the base stimulation frequency will again be lowered by the rest frequency control algorithm, making it possible to return the stimulation frequency to a level which will again induce extrasystole events.

A similar oscillation phenomenon appears in the effort phase of the patient, with the devices equipped with a stimulation frequency that is determined as a function of patient activity. Such a stimulation frequency control is also referred to herein as an "enslaved frequency". In these devices, the enslaved frequency control algorithm adjusts the stimulation frequency to the activity level of the patient, and, in particular, increases the stimulation frequency with the level of effort up to a maximum frequency limit. If the patient presents a tachy-dependent extrasystole, an acceleration of the stimulation frequency can be a factor favoring the appearance of undesirable extrasystoles. This, in turn, will trigger a monitoring function in the control algorithm which causes the device to return to a lower enslaved frequency, with an ensuing rise in the stimulation frequency due to the patient's activity level, which again induces extrasystoles, and so on.

OBJECTS AND SUMMARY OF THE INVENTION

It is, therefore, an object of the present invention to provide a device that is capable of detecting the appearance of such undesirable extrasystole oscillation phenomena and to place the device in a state which will inhibit the appearance of such undesirable phenomena.

Broadly, one aspect of the invention is directed to a device of a general type as described, for example, in the EP-A-0

672 433 and corresponding U.S. Pat. No. 5,645,576, which includes: means for determining an activity level of the patient bearing the device, including analyzing the activity and discriminating between a rest phase, a normal activity phase and an effort phase; means for stimulating at least one cardiac cavity, capable of delivering to the heart pulses at a base stimulation frequency determined by the device; and means for adjusting the base stimulation frequency according to the determined activity level, including lowering the base stimulation frequency to an initial base stimulation frequency minimum level limit during a determined rest phase.

To detect brady-dependent extrasystoles and to alleviate the consequences of such brady-dependent extrasystoles, the device also includes: means for detecting the occurrence of extrasystoles, means for evaluating a corresponding rate of occurrence of such extrasystoles, and means for diagnosing a brady-dependent extrasystole condition and increasing the minimum level limit of the base frequency when the extrasystole rate exceeds a predetermined threshold during the detected rest phase.

Advantageously, an increase in the minimum base frequency level is maintained at least for the entire duration of the rest phase, and preferably is not restored to its former or initial value until the detection of an effort phase, subsequent to the rest phase. Thus, extrasystoles are avoided.

Another aspect of the invention is directed to a device of the aforementioned general type which includes means for detecting tachy-dependent extrasystoles and preventing the undesirable effects of such tachy-dependent extrasystoles. Such a device thus includes means for detecting an occurrence of extrasystoles during an effort phase, means for evaluating a corresponding extrasystole rate, and means for diagnosing a tachy-dependent extrasystole condition and decreasing an enslaved frequency maximum level limit when the extrasystole rate exceeds a predetermined threshold during the aforementioned effort phase.

Advantageously, the reduction in the enslaved frequency maximum level is maintained at least for the entire duration of the aforementioned effort phase, and is preferably not restored to its former or its initial value until the detection of a rest phase, subsequent to the aforementioned effort phase.

BRIEF DESCRIPTION OF THE DRAWINGS

Other features, characteristics and advantages of the present invention will appear to a person of ordinary skill in the art in view of the following detailed description of a preferred embodiment of the invention, made with reference to the drawings annexed, in which.

DETAILED DESCRIPTION OF THE INVENTION

Figure 1:
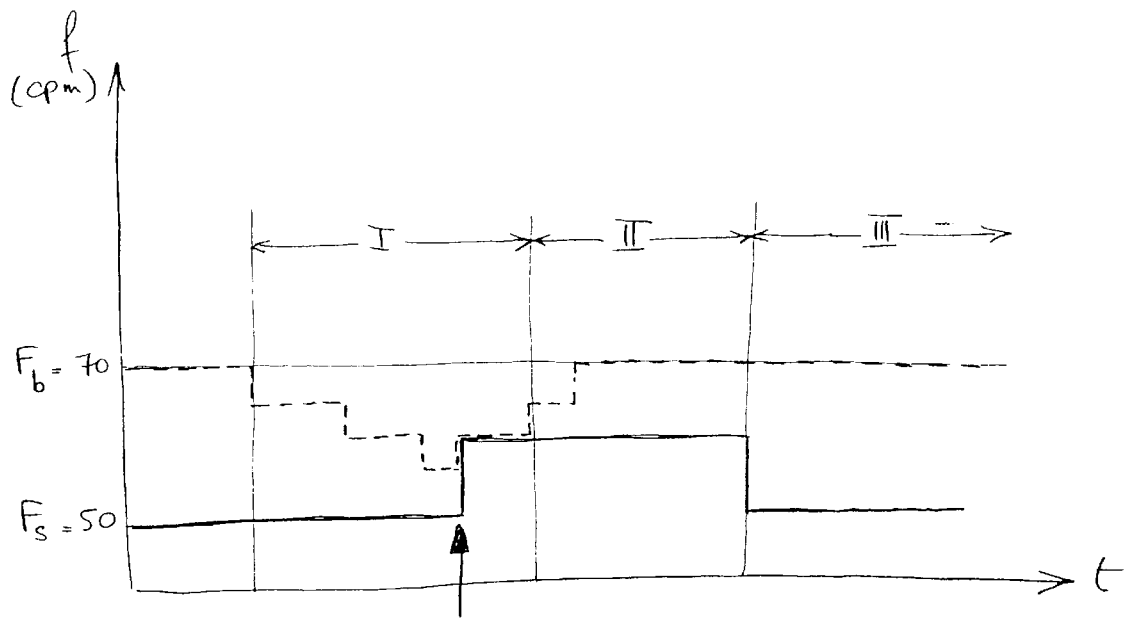
FIG. 1 illustrates diagnosing and treating a brady-dependent extrasystole.

In a known manner, the device of the present invention monitors events occurring in the atrial and ventricular cavities of the heart, and detects the appearance of either AES or VES extrasystoles in either cavity. See, e.g., EP-A-0 755 696 and its counterpart U.S. Pat. No. 5,713,928, commonly assigned herewith to ELA Médical, which describe one such device and manner of detecting these extrasystoles which is useful in implementing the present invention.

The device also determines an extrasystole rate in the event of the appearance of successive extrasystoles, this rate being defined, for example, as the relationship over a given period of time between the number or count of extrasystole events and the detected number of cardiac cycles. The extrasystole rate is then compared to a threshold, and the device will diagnose that there is an extrasystole condition present, either of the brady-dependent or tachy-dependent type, when the extrasystole rate exceeds the threshold. The threshold may typically be defined as the presence of five detected extrasystoles events over the course of thirty-two successive cardiac cycles or as a minimum ratio. Other values, of course, may be used.

Alternatively, it is also possible to count the number of extrasystoles occurring during a given period of time and to diagnose an extrasystole condition when the counter reaches a predetermined value before the end of the time period. In this case, the threshold is the predetermined value.

The invention primarily proposes to correlate the extrasystole rate determined by the device with the stimulation frequency when the stimulation frequency varies according to the activity of the patient. Optionally, the correlation includes identifying the cardiac rate or frequency at which the extrasystole condition is diagnosed and altering the appropriate stimulation rate limit for the appropriate activity phase, so that the stimulation rate delivered is maintained within a cardiac rate range which does not produce an excessive extrasystole rate.

The manner in which brady-dependent extrasystoles are treated will now be described with reference to FIG. 1. Phase I corresponds to a prolonged rest phase of the patient, typically either a diurnal or a night sleep period. Such a prolonged rest phase can, for example, automatically be diagnosed starting from the signal delivered by a sensor which responds to the respiratory rhythm of the patient and/or by another type of sensor, for example, an activity sensor, i.e., an accelerometer integrated into the device case (a so-called "sensor G").

One may refer, for example, to EP-A-0 719 568 and its U.S. Pat. No. 5,622,428 which describes a suitable process of determining "sensor activity criteria" that can distinguish between rest phases, either night or diurnal rest phases, and other activity phases of the patient bearing the apparatus, using, in particular, a minute ventilation sensor. One also may refer to EP-A-0 750 920 (and its corresponding U.S. Pat. No. 5,722,996) and EP-A-0 770 407 (U.S. Pat. No. 5,766,228), which describe medical devices that use information combined from a physiological sensor and a physical sensor, in particular, a minute ventilation sensor and an accelerometer, to determine an activity state or a rest state of the patient. These patents are also commonly assigned herewith to ELA Médical.

In FIG. 1, phase I thus corresponds to a rest period as determined by the device. During this prolonged rest period, the base frequency Fb is gradually lowered, from the value Fb=70 bpm, for example, to an initial programmed limit value, namely, a minimum stimulation value or sleep frequency Fs=50 bpm, for example, which value constitutes the minimum level reachable by the base frequency Fb.

The progressive reduction of the base frequency Fb is operated, for example, in the manner described in EP-A-0 672 433 and U.S. Pat. No. 5,645,576 which is hereby incorporated by reference.

During the time in which the base frequency Fb is progressively lowered, the device continues to determine and evaluate the extrasystole rate. At the time D, corresponding to a confirmed diagnosis of a brady-dependent extrasystole, the device modifies the minimum frequency Fs to a value or level corresponding to a frequency step that is slightly higher than the frequency step in existence when the extrasystole diagnosis occurred. Thus, the cardiac rate corresponding to the rate at which the extrasystole rate exceeds the predetermined threshold is used as a "trigger" to increase the minimum base level limit. The reference to "frequency step" is to a particular frequency in the case of a stepwise increment of the stimulation frequency. In the illustrated example, Fs is increased from the initial programmed limit of 50 bpm to 60 bpm, because the extrasystole diagnosis occurred when the frequency step was at the 55 bpm range, and the step between frequencies was 5 bpm.

Accordingly, the base frequency Fb will no longer reach the lower initial base frequency range which resulted in generating the brady-extrasystoles.

When prolonged rest phase I is completed, and the patient resumes a normal activity phase, i.e., phase II, the base frequency routinely increases, for example, to its programmed value, Fb=70 bpm. The sleep frequency Fs, still set to the higher value of Fs=60 bpm in this example, will then be reset to its previously programmed or initial limit value, Fs=50 bpm, on the next effort phase detected by the device, i.e., phase III.

It should be understood, however, that the brady-dependent extrasystole phenomenon is highly variable for any given patient, and can change according to any given set of circumstances, day-to-day and week-to-week. For example, a prolonged rest period may be either a siesta or a night sleep period, with different results. Also, the manner in which and the amount by which the sleep frequency Fs is adjusted to prevent the appearance of brady-dependent extrasystoles on one particular occasion is not necessarily the same used to prevent their appearance on the next occasion of a confirmed extrasystole diagnosis.

Figure 2:
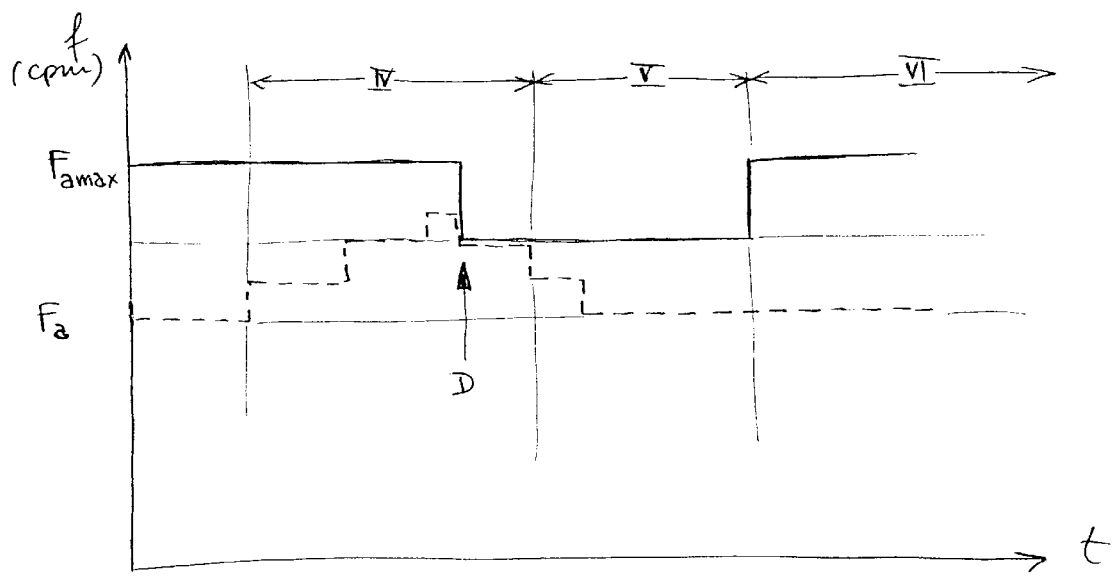
FIG. 2 illustrates diagnosing and treating a tachy-dependent extrasystole.

The invention is applicable in the same way, mutatis-mutandis, to the treatment of tachy-dependent extrasystoles, as illustrated in FIG. 2. In this regard, the control algorithm, in a manner known to persons skilled in the art, is able to adapt the stimulation frequency—herein referred to as the enslaved frequency Fa—to the activity of the patient, in particular, to increase the stimulation frequency in the event of patient effort. The enslaved frequency Fa is limited to a maximum value Famax, which is typically programmed to an initial limit value by the physician at the time of implantation.

In the case of a detected patient effort, phase IV (FIG. 2), the enslaved frequency Fa increases gradually, without being able to exceed Famax. In the case of a patient presenting a tachy-dependent extrasystole diagnosed at moment D, the device will lower the maximum enslaved frequency limit Famax to a frequency that is slightly lower than the frequency at which the extrasystole diagnosis occurred. This control algorithm also uses the stepwise adjustment process as discussed above in the brady-dependent extrasystole example. When the effort phase ceases and the patient returns to a condition of normal activity, phase V, the enslaved frequency Fa decreases correlatively, e.g., stepwise. Once the enslaved frequency maximum limit Famax is lowered, however, the enslaved frequency maximum limit Famax is maintained at its new value throughout the patient's effort, and is reset to its previously programmed or initial limit value only when a phase of rest, phase VI, is detected. As in the case of brady-dependent extrasystoles, tachy-dependent extrasystoles are not a systematic and repetitive phenomenon, but can vary for the same patient according to the conditions or periods considered.

It should be understood that the present invention is preferably implemented in the form of software that performs one or more of the control functions described herein. Suitable rate-responsive pacemakers which may be modified to include such software, programmed at the time of construction or post-implantation by downloading the instructions via telemetry, include the Talent and Brio model pacemakers available from ELA Médical S. A., Montrouge, France.

One skilled in the art will appreciate that the present invention can be practiced by other than the described embodiments, which are presented for purposes of illustration and not of limitation.

We claim:

1. An active implantable medical device, including:

means for analyzing a signal representative of patient activity, discriminating between a rest phase, a normal activity phase and an effort phase, and determining an activity level of a patient;

stimulation means for delivering to at least one cardiac cavity pulses at a base frequency; and means for adjusting the base frequency according to the determined activity level, said base frequency having an initial base frequency minimum level during a determined rest phase;

wherein the improvement comprises:

means for detecting an occurrence of extrasystole events and determining therefrom a corresponding extrasystole rate; and means for comparing the determined extrasystole rate to a predetermined threshold during said rest phase and increasing the base frequency minimum level to an increased level above the initial base frequency minimum level in response to the extrasystole rate exceeding said predetermined threshold.

2. The device of claim 1, wherein the comparing means operates to maintain the base frequency minimum level at the increased level at least for the entire duration of the said determined rest phase.

3. The device of claim 2, further comprising means for monitoring a cardiac rate and determining a trigger cardiac rate when the extrasystole rate exceeds said predetermined threshold, and wherein the comparing means operates to increase the base frequency minimum level to a frequency level that is set above the trigger cardiac rate.

4. The device of claim 2, wherein the comparing means operates not to reset the base frequency minimum level to said initial base frequency minimum level until said determining means determines an effort phase subsequent to said determined rest phase.

5. The device of claim 1 wherein the detecting means further comprises means for counting the number of detected extrasystole events during a time period and determining when the count exceeds a predetermined count.

6. An active implantable medical device including:

means for analyzing a signal representative of patient activity, discriminating between a rest phase, a normal activity phase and an effort phase, and determining the activity level of a patient;

stimulation means for delivering to at least one cardiac cavity pulses at an enslaved frequency; and means for adjusting the enslaved frequency according to the determined activity level, said enslaved frequency having an initial maximum level during a determined effort phase;

wherein the improvement comprises:

means for detecting cardiac events and an occurrence of extrasystole events and determining therefrom a corresponding extrasystole rate; and means for comparing the extrasystole rate to a predetermined threshold during said determined effort phase and reducing the enslaved frequency maximum level to a reduced level in response to the extrasystole rate exceeding said predetermined threshold.

7. The device of claim 6, further comprising means for monitoring a heart frequency and determining a trigger heart frequency at which the extrasystole rate exceeded the predetermined threshold, and wherein said comparing means further comprises means for reducing the enslaved frequency maximum level to a frequency below the trigger heart frequency.

8. The device of claim 7, wherein the comparing means operates to maintain the enslaved frequency maximum level at the reduced level at least for the entire duration of said determined effort phase.

9. The device of claim 8, wherein the comparing means operates not to reset the enslaved frequency maximum level to its maximum level value until said determining means determines a rest phase subsequent to said effort phase.

10. The device of claim 7, further comprising means for monitoring cardiac activity and determining therefrom a count of cardiac cycles and the extrasystole rate is determined as a ratio of extrasystole events detected during said count of cardiac cycles to said count.

* * * * *

UNITED STATES PATENT AND TRADEMARK OFFICE
CERTIFICATE OF CORRECTION

PATENT NO. : 6,408,209 B1
DATED : June 18, 2003
INVENTOR(S) : Anne Bouhour, Marcel Limousin and Jean Luc Bonnet It is certified that error appears in the above-identified patent and that said Letters Patent is hereby corrected as shown below:

Title page,
Item [54], Title, delete "BRADY-AND/OR" and insert -- BRADY - AND/OR --;

Column 1,
Line 67, after "heart" insert -- - --;

Column 4,
Line 9, after "detected" delete "extrasystoles" and insert -- extrasystole --;
Line 38, after "its" insert -- corresponding --;

Signed and Sealed this

Nineteenth Day of October, 2004

JON W. DUDAS
*Director of the United States Patent and Trademark Office*